United States Patent
Roberts et al.

(10) Patent No.: US 8,092,370 B2
(45) Date of Patent: Jan. 10, 2012

(54) DIRECT VISUALIZATION ROBOTIC INTRA-OPERATIVE RADIATION THERAPY APPLICATOR DEVICE

(75) Inventors: Walter A. Roberts, Brainerd, MN (US); Brooke Schumm, III, Ellicott City, MD (US)

(73) Assignee: Sriort, LLC, Baltimore, MD (US)

( * ) Notice: Subject to any disclaimer, the term of this patent is extended or adjusted under 35 U.S.C. 154(b) by 0 days.

(21) Appl. No.: 12/532,123

(22) PCT Filed: Sep. 19, 2008

(86) PCT No.: PCT/US2008/077100
§ 371 (c)(1),
(2), (4) Date: Jun. 21, 2010

(87) PCT Pub. No.: WO2009/039428
PCT Pub. Date: Mar. 26, 2009

(65) Prior Publication Data
US 2010/0280374 A1 Nov. 4, 2010

Related U.S. Application Data

(60) Provisional application No. 60/973,545, filed on Sep. 19, 2007, provisional application No. 61/098,225, filed on Sep. 18, 2008.

(51) Int. Cl.
*A61F 5/00* (2006.01)
(52) U.S. Cl. .......................................................... 600/38
(58) Field of Classification Search .................. 600/1–8; 128/897, 898
See application file for complete search history.

(56) References Cited

U.S. PATENT DOCUMENTS
5,427,097 A * 6/1995 Depp ............................ 600/427
(Continued)

FOREIGN PATENT DOCUMENTS
CN  201085857 Y  7/2008
(Continued)

OTHER PUBLICATIONS
Bernier, Partial Irradiation of the Breast: Old Challenges, New Solutions, 15 Breast 466-475 (Elsevier 2006).

*Primary Examiner* — Samuel Gilbert
(74) *Attorney, Agent, or Firm* — Brooke Schumm, III; Daneker, McIntire, Schumm

(57) ABSTRACT

This invention proposes a robotic applicator device to be deployed internally to a patient having a capsule (also referred to as a cassette) and aperture with a means of alternately occluding and exposing a radioactive source through the aperture. The capsule and aperture will be integrated with a surgical robot to create a robotic IORT (intra-operative radiation therapy) applicator device as more fully described below. The capsule, radiation source, and IORT applicator arm would be integrated to enable a physician, physicist or technician to interactively internally view and select tissue for exposure to ionizing radiation in sufficient quantities to deliver therapeutic radiation doses to tissue. Via the robotic manipulation device, the physician and physicist would remotely apply radiation to not only the tissue to be exposed, but also control the length of time of the exposure. Control means would be added to identify and calculate margin and depth of tissue to be treated and the proper radiation source or radioactive isotope (which can be any particle emitter, including neutron, x-ray, alpha, beta or gamma emitter) to obtain the desired therapeutic effects. The invention enables stereotactical surgery and close confines radiation therapy adjacent to radiosensitive tissue.

62 Claims, 1 Drawing Sheet

U.S. PATENT DOCUMENTS

| | | |
|---|---|---|
| 6,241,670 B1 * | 6/2001 | Nambu .................. 600/427 |
| 6,270,464 B1 | 8/2001 | Fulton |
| 6,537,195 B2 | 3/2003 | Forman |
| 6,713,773 B1 | 3/2004 | Lyons |
| 6,799,075 B1 | 9/2004 | Chornenky et al. |
| 6,889,695 B2 | 5/2005 | Pankratov |
| 7,018,371 B2 | 3/2006 | Forman |
| 7,041,046 B2 | 5/2006 | Forman |
| 7,154,991 B2 | 12/2006 | Earnst |
| 7,354,433 B2 | 4/2008 | Pierce |
| 7,496,174 B2 | 2/2009 | Gertner |
| 7,564,946 B2 | 7/2009 | Gertner |
| 7,620,147 B2 | 11/2009 | Gertner |
| 7,680,244 B2 | 3/2010 | Gertner |
| 7,693,260 B2 | 4/2010 | Gertner |
| 2001/0009970 A1 | 7/2001 | Chornenky |
| 2003/0192557 A1 | 10/2003 | Krag |
| 2005/0027194 A1 | 2/2005 | Adler |
| 2005/0070753 A1 | 3/2005 | Forman |
| 2005/0124844 A1 | 6/2005 | Forman |
| 2005/0226377 A1 | 10/2005 | Wong |
| 2005/0276377 A1 | 12/2005 | Carol |
| 2006/0133575 A1 | 6/2006 | Gutman |
| 2008/0144771 A1 | 6/2008 | Gertner |
| 2008/0219402 A1 | 9/2008 | Wu |

FOREIGN PATENT DOCUMENTS

| | | |
|---|---|---|
| WO | WO9413205 | 6/1994 |
| WO | WO0113060 | 2/2001 |

* cited by examiner

DIRECT VISUALIZATION ROBOTIC INTRA-OPERATIVE RADIATION THERAPY APPLICATOR DEVICE

CONTINUATION DATA

This application claims benefit of and as may be required is a continuation-in-part for any national stage, including the United States, of U.S. Provisional application 60/973,545 entitled "Direct visualization Robotic Intra-Operative Radiation Therapy Applicator Device" filed on Sep. 19, 2007 and from which benefit is claimed for PCT/US2008/077100 of the same name, and a U.S. provisional application 61/098,225 of the same name filed on Sep. 18, 2008, and a U.S. Provisional Application of this name filed on Sep. 18, 2009, all of which are incorporated by reference. This is a section 371 entry as well as a continuation-in-part of PCT/US2008/077100.

FIELD OF INVENTION

This invention relates to radiation cancer treatment by a mobile miniature capsule or cassette containing a radioactive source deployed internally to a patient which is robotically manipulated having an openable aperture to allow radiation emission to more precisely destroy tumors, especially those on organs, and to obtain a quality margin while not destroying underlying healthy, essential tissue. The invention enables close confines radiation therapy. The invention enables the practical use of intraoperative irradiation, with alpha, beta and neutrons, x-ray, gamma or a combination thereof.

SUMMARY

This invention proposes a robotic applicator device to be deployed internally to a patient having a capsule (also referred to as a cassette) and aperture with a means of alternately occluding and exposing a radioactive source through the aperture. The capsule and aperture will be integrated with a surgical robot to create a robotic IORT (intra-operative radiation therapy) applicator device as more fully described below. The capsule, radiation source, and IORT applicator arm would be integrated to enable a physician, physicist or technician to interactively internally view and select tissue for exposure to ionizing radiation in sufficient quantities to deliver therapeutic radiation doses to tissue, while avoiding exposure to personnel. Via the robotic manipulation device, the physician and physicist would remotely apply radiation to not only the tissue to be exposed, but also control the length of time of the exposure. Control means would be added to identify and calculate margin and depth of tissue to be treated and the proper radiation source or radioactive isotope (which can be any particle emitter, including neutron, x-ray, alpha, beta or gamma emitter) to obtain the desired therapeutic effects.

This invention described herein comprises the integration of a radiation application device with a surgical robotic machine for the purpose of allowing a novel form of radiotherapy treatment internally to a person having a cancer or other neoplasm consisting of one or more tumors by attaching and integrating a capsule containing a radiation producing isotope or x-ray or particle generator with an occlusive shielding mechanism to permit the introduction, visualization and aiming of a precise radiation field to expose the cancerous and benign tumors to a lethal dose of radiation under the remote guidance of the surgical robot systems. This invention will permit, under robotic control, the selection of a capsule, attachment to the surgical robotic arms and introduction of the radiation into the patient under direct and imaging guided visualization for the purpose of exposing cancerous tissues, intra-operatively to doses of radiation by exposing the tumor cells to a radiation field for an adequate amount of time to render them incapable of further growth and thus, limiting further growth of the diseased tumor cells.

As this invention is intended to be used intra-operatively, surgeons skilled in the art of cancer surgery, together with radiation oncologists and medical physicists skilled in the art of using and delivering radiation treatments will use the invention cooperatively at the time of surgical removal of the tumor and at subsequent intervals as may be necessary to deliver radiation treatments intra-operatively as part of a planned surgical procedure to deliver curative doses of radiation to tumors. The invention, using imaging techniques such as ultrasound, MRI, CT, PET or PET/CT or some combination of medical imaging guidance, a priori or contemporaneously with the surgical procedure to guide and direct the radiation oncologist in the correct and accurate placement of the radiation field inside the patient and timing of tissue exposures to produce a curative dose of radiation without delivering doses to uninvolved tissues to minimize, to the greatest extent possible the complications associated with radiation treatment and delivery. The invention described herein will allow the operator to identify neoplastic tissue (benign or cancerous) of interest to the operator via medical imaging as described above, real time guidance via spatial depiction of the key anatomical landmarks at the time of insertion of the capsule for irradiation intra-operatively, real-time depiction in 3-dimensions on the imaging display system of the precise position of the applicator through the surgical robots' positioning reporting technologies and under direct visualization using visible light techniques and permit the operator to precisely position the intraoperative radiotherapy capsule in such a way, within the human body, using the surgical robotic manipulator arms under remote control of the robot by the physician, to deliver the proper type and exposure of radiation to the neoplastic tumors, thus enhancing the probability of curing and/or better managing the disease.

BACKGROUND

Traditionally, intraoperative radiation therapy has been delivered via large, cumbersome linear accelerators and via injections of radioactive substances, both of which can cause substantial collateral damage and resultant morbidity and have not been shown to substantially improve outcomes. A significant and longstanding problem with many cancers, such as ovarian cancer, is that upon resection (surgery), it is difficult to obtain what is referred to as a clear margin, or optimal debulking, that is a complete surgical removal of all cancer, including microscopic cancer. As a result, residual cancer cells frequently remain, and may (and often do) break off from the primary cancer and migrate to other locations which are difficult to reach and destroy. Moreover, the other sites to which the cancer cells may migrate (metastasize), are often adjacent to and on sensitive organ tissue, even if they have not invaded the organ at the time of discovery. The metastatic cancer cells will then begin to grow using the local blood supply of the new site of involvement, eventually compromising organ function, and ultimately destroying the organ, frequently resulting in death.

Traditional external beam radiation therapy techniques frequently are ineffective in treating such localized metastases due to the relative toxicity of radiation delivered to the involved organ. A dose of radiation sufficient to destroy the cancer will be likewise fatal to the involved tissue or organ at issue due to the inability in the non-operative setting to deliver a specific dose to only the cancerous lesions. The inability of external beam radiotherapy to precisely target a small metastatic lesion is well documented and relates to a.) inability to visualize small lesions on CT/MR/PET with high precision b.) inability to identify and track organ motion in real time for the period needed to precisely target a small cancerous lesion c.) inability to restrict the external beam dose using conventional, conformal, IMRT, cyberknife or tomography techniques to the cancerous lesions enough to deliver sufficient dose to the tumor without unacceptable normal organ damage.

The statistics supporting complete removal (i.e. optimal surgical excision) are very compelling. Research has demonstrated that for locally advanced ovarian cancer, the prognosis is dismal and for Stage III ovarian cancers, comprising 51% of all ovarian cancer cases, as an example, the five year survival rate for optimally debulked cancers (no gross residual disease apparent), is between 21% and 5%, and there has been little change in mortality in the last 25 years, despite advances in chemotherapy and surgical techniques.[Gunderson]

The volume of residual disease is an important prognostic indicator supported by numerous studies demonstrating the value of cytoreductive surgery (ie the complete removal of all visible cancer cells), both in primary and secondary procedures. That is, the larger the volume of residual disease, the poorer the prognosis. Cytoreductive procedures have been shown to prolong progression free survival intervals and overall survival for patients with disease less than 1 cm remaining. For these patients, treatment with chemotherapeutic agents has been helpful, but ovarian cancer progression and death remains high. The value of reducing residual disease has been shown to be important. With no residual disease, median survival was 39 months, with <0.5 cm residual disease, median survival dropped to 29 months, with residual disease between 0.5 cm and 1.5 cm, 18 months and less than 11 months for residual disease greater than 1.5 cm. [Griffiths]

Radiation therapy is a well known treatment modality for neoplastic (cancerous) disease. Radiation therapy has been tried without success in treating abdominal cancers in general, due the inability to deliver dose specifically to sites of residual disease without producing unacceptable morbidity and mortality due to the highly sensitive normal tissues in the abdomen. Intraoperative radiation therapy has not been widely adapted due to the previous inability to precisely deliver radiation to tumors while minimizing dose to normal tissues.

Other attempts at delivering radioactive seeds include placing catheters, but absent a robotic arm device and the dose delivery apparatus contemplated in this invention and the real time dosimetry and source selection during the surgical procedures, the delivery methods are inflexible and cannot be precisely guided in the way that the invention proposes, and cannot be rapidly repositioned during the course of the treatment. In other words, once a catheter has been placed, it is fixed and immobile absent a second operation, while the proposed invention will allow immediate and precise positioning at the time of the surgery, allowing flexibility and precision unobtainable with the traditional methods of catheter placement.

This invention proposes to be integrated with recent technologies developed and owned by Intuitive Surgical, Inc., called the DaVinci Robotic Surgery Device, a form of intra-operative robotic surgical device, and more generally to intra-operative robotic surgical devices, including a Bright Lase Ultra Laser™ surgical laser mad by QPC Lasers of Sylvan, Calif. Examples of technology related to intra-operative robotic surgical devices can be found in "Performing cardiac surgery without cardioplegia," Evans et al, U.S. Pat. No. 6,468,265, Oct. 22, 2002; "Manipulator positioning linkage for robotic surgery," Blumenkranz et al, U.S. Pat. No. 6,246,200, Jun. 12, 2001, "Master having redundant degrees of freedom," Salisbury, Jr. et al, U.S. Pat. No. 6,684,129, Jan. 27, 2004; and devices illustrating automated control such as "Minimally invasive surgical training using robotics and tele-collaboration," Wang et al, U.S. Pat. No. 7,413,565, Aug. 19, 2008, the descriptions in which are adopted by reference to illustrate surgical robotic intra-operative surgical devices and integrated surgical robotic intra-operative systems. The field of radiation oncology has changed markedly with the introduction of imaging based radiation therapy treatment planning in the early 1990s for external beam radiation therapy. An example is the Mobitron™ now manufactured by Philips which uses a linear acceleration radiation system. The technologies that make this possible have allowed the design of precision radiation fields to treat cancers in ways that were previously not possible, but have a clumsy aspect because of their size. which renders them unable to be precisely manipulated into a position where the therapeutic beam can be optimally aimed to provide maximum therapeutic advantage: ie, the targeting of high risk tumor areas while avoiding dose to uninvolved tissue. There has been a long felt need to be able to precisely target cancers and other tumors in the intra-operative setting as well. The development of the DaVinci style intra-operative surgical device and like devices (also more generically referred to as a "surgical robot") creates a new avenue to exploit in the pursuit of this goal, which avenue is the subject of this invention.

For the purposes of this invention, a device which proposes to stabilize the patient and then robotically undertake surgery and treatment with the physician operating at least one robotic device or arm shall be referred to as a surgical robot. For the purposes of this invention, a surgical robot which uses the radiotherapy capsule or cassette and related guidance systems as an attachment to a robotic manipulator arm shall be referred to as a surgical robotic intra-operative radiation therapy device, or SRIORT.

This invention is unique in that the device allows the physician to identify and deliver a lethal radiation dose to one or more tumor sites at the time of surgery in real time under direct visualization. By contrast, under the present art, an applicator is put in place and at a later date and time post-operatively deliver radiation using devices such as the Mammosite® balloon/catheter type devices or a flat square of material containing afterloading catheters through which a radioactive source may be placed at a later date and time.

As previously stated, intraoperative radiation post-surgical therapy and therapy during surgery have been delivered via large, cumbersome linear accelerators and via injections of radioactive substances, both of which can cause substantial collateral damage and resultant morbidity and have not been shown to substantially improve outcomes.

Other approaches are inflexible and cannot be precisely guided in the way that the invention proposes, and cannot be rapidly repositioned during the course of the treatment. In other words, once a catheter has been placed, it is fixed and immobile absent a second operation, while the proposed invention will allow immediate and precise positioning at the time of the surgery, allowing flexibility and precision unobtainable with the traditional methods of catheter placement.

An additional benefit is that the proposed invention will permit the introduction of intra-operative radiation therapy during a closed laparoscopic procedure rather than requiring an open procedure as is presently required with linear accelerator based intra-operative techniques.

This invention proposes a new addition to IORT that enables a much more highly specific targeted treatment of cancerous tissue and can direct radiation from different angles as needed to minimize vital organ damage while applying lethal doses of radiation localized to the cancerous lesion.

The SRIORT device will overcome disadvantages in the present art by combining the ability to deliver precise, robotically performed surgery using a surgical robot, followed by the ability, in the operating room, using the same surgical robot, to attach the SRIORT device containing a radioisotope with high specific activity and energy characteristics, combined with a movable aperture, aiming device and dosing and timing logic which will enable the delivery of radiation in a highly localized manner to treat areas of known or suspected residual disease while sparing normal tissue radiation dose, thus creating a substantial therapeutic advantage. This device will combine PET/CT/MR and direct imaging modalities, including video imaging, intraoperative ultrasonic imaging, and tactile response sensors to precisely identify the areas to be treated, the depth of desired treatment and the radiation dose needed.

As the SRIORT device will permit the intra-operative placement of a radiation field directly on a tumor site, in real time, without the need for an open laparotomy as is the case in conventional intraoperative radiotherapy, and at the same time the robotic component will permit the surgeon and radiation oncologist to safely place the desired treatments in real time in the operating room with minimal to no personnel exposure to ionizing radiation, this invention represents a dramatic step forward in the art of radiation therapy. It will eliminate the need for open surgery, utilize minimally invasive surgery, and will reduce the need for a second operation for traditional catheter based brachytherapy.

The application of the invention also contemplates delivery of radiation to what have been viewed as "inoperable" cancers because of proximity to critical tissue. This invention enables stereotactical intervention by radiation in a precise manner adjacent to radiosensitive tissue not ordinarily amenable to radiation therapy without lethal or undesired consequences.

OBJECTIVES OF THE INVENTION

A first objective of the invention is to enable non-surgical precise improvement of margins by intra-body irradiation which cannot be safely done by a human in close proximity to the capsule and tissue to be irradiated.

A second objective is to enable visual examination of tissue adjacent to surgically removed tissue, and on a real-time basis, irradiate tissue that needs to be eliminated, or irradiate tissue to increase the margin from removed tissue.

A third objective is to enable removal of tissue to precise depths by irradiation inside the patient's body, including while visually examining such tissue, so that "inoperable," meaning tissue that is radiosensitive, or dangerous to excise, can be precisely removed or avoided.

A fourth objective is to enable visualization and removal of small lesions, including those detected on CT/MR/PET, with high precision.

A fifth objective is to identify and track organ or tissue motion in real time for the period needed to precisely target a small cancerous lesion, and adjust irradiation to coordination with organ or tissue motion.

A sixth objective is to restrict irradiation to benign, malignant, or cancerous lesions enough to deliver sufficient dose to the tumor without unacceptable normal organ damage, and avoid the imprecision and collateral damage from the inability to restrict the external beam dose using conventional, conformal, IMRT, cyberknife or tomography techniques to the precise lesion and desired margin.

A seventh objective is to use the increased velocity and accuracy with which a surgical robot can move to minimize invasive time that would be required and simultaneously decrease unnecessary time of exposure to radiation.

DESCRIPTION OF THE INVENTION

Figure 1:
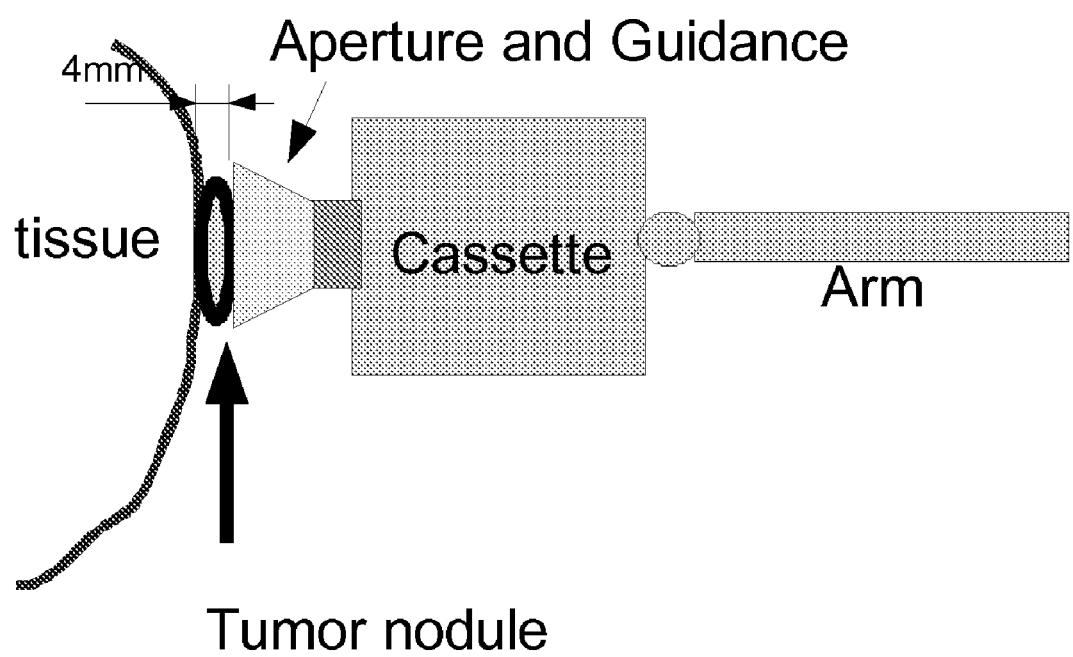
FIG. 1 shows the relative positions of the body tissue (1) with the tumor nodule (2) (an example of 4 mm. depth is shown) which is being targeted disposed on said tissue. A simplified diagram of a shroud (3) containing a locator mechanism is shown over the tissue, with the cassette (4) containing the radioactive substance, and the general disposition of the cassette on a robotic arm (5).

The preferred mode of invention proposes to first select an interchangeable irradiating capsule with a shutter as set forth below. Based on the depth and size of tissue to be treated, a radiation source will be selected for placement in the capsule and mounted on the robotic arm of the SRIORT. The arm would then be moved to the proper location for irradiation of the tissue, under direct visualization, with or without assistance from alternative imaging modalities or any combination of these.

Expanding on the above, the key invention components are:

- A radiation source
- A capsule/arm with an aperture opening to a cavity containing the radiation source with certain control electronics and devices designed to be connected to the surgical robot and inserted into the patient's body through the laparoscopic/surgical robotic incisions
- For a lesion, tumor, tissue, or organ, a mechanism for displaying pre-operative medical imaging, fused pre-operative medical imaging, including CT, MRI, Ultrasound, functional MRI, PET, PET/CT and nuclear medical scanning in the operating room in real time visible to the manipulation station of the surgical robot preferably on a video screen or computer monitor or other means for display.
- A mechanism for identifying and tracking the real time coordinates of the radiation source capsule within the body and displaying the 3-dimensional location of the capsule on the pre-operative imaging with a projection of the presently programmed radiation field distribution on the images and a control means such as a general purpose computer to make real-time updates to the tissue position relative to the surgical robot, avoiding overdoses to desired tissue.
- A mechanism for tracking, visually, preferably on a video screen, computer monitor, or means for display the internal position of the capsule within the body and for advancement and positioning under direct visualization using visible, infrared and ultraviolet light or any combination of these.

A mechanism for identifying the tumor, and tumor depth (using a combination of the above or ultrasonic echoes)

A mechanism for setting an aperture size, accepting a desired dose and calculating the exposure time based on the selected radiation source physical parameters and characteristics.

A mechanism for activating the now properly positioned radioactive source in the cavity to deliver the desired radiation dose, and field size and shape to the desired volume of the tumor while preventing exposure to the operating room personnel. Normally this would mean an electromechanical actuator opening a closed shutter in the capsule. However, a mechanical connection could be made so that an actuator, such as a pin, in the surgical robot arm actually activates the shutter to open. A spirally opening and closing iris shutter of the style used in a camera, or a simple door mechanism can provide an adjustable aperture.

A mechanism for identifying and tracking the real time coordinates of the radiation source capsule within the body and displaying the 3-dimensional location of the capsule on the pre-operative imaging, a post-radiation report to show radiation field distribution on the images, on for instance, a video screen, computer monitor or means for display, and probable damage to irradiated tissue.

These components and mechanisms will be described in detail below.

The application of the invention would be as follows for cancers:

The physician would have pre-imaged the patient's body according to standard medical procedures to locate the tumor and any other areas of suspected cancer activity, sometimes known as "hot spots". These are areas that are identifiable in a variety of medical imaging modalities, including PET, CT, MRI and nuclear medicine scans. The physicians would have visually identified any other areas of suspected cancer involvement during the course of surgical intervention.

The physician will then make an incision in the abdomen and the SRIORT is activated. The SRIORT has a television camera mounted on a robotic arm. The SRIORT has accessories mounted on a robotic arm and are controlled by remote control. The surgical SRIORT is then used to incise the interior membranes and a cutting implement is used to perform a resection by the physician. The surgeon can cauterize and clean as needed and ultimately view the remaining tissue through the camera on the SRIORT arm, and in conjunction with medical imaging as described above, determine what further areas need radiation treatment.

In the case of ovarian cancer, when the maximum surgical debulking possible has been obtained, frequently, studs of disease remain which involve the surface of the liver, the diaphragm and areas of the bowel. It is not possible to treat these areas generally with external beam (whole abdominal radiation therapy), conventional brachytherapy or loose isotope therapy or conventional intraoperative radiation therapy using accelerators due to the inability to deliver a precisely enough targeted and sufficient dose of radiation to eliminate cancer metastases without causing substantial morbidity and even mortality, or exposing operating room personnel to unacceptably high exposures to radiation.

Based on the depth of tissue desired to be penetrated and the desired dose to be delivered, a particular radiation source, which may be a radioisotope or device generated radiation (x-rays), of appropriate emission type, energy and strength would be selected for placement in the capsule on the SRIORT arm. This capsule would be either permanently mounted on the SRIORT arm or preferably would be an interchangeable module to accommodate differing physical characteristics of radiation sources. The capsule must be designed to balance size of the device with necessary shielding for both direction and size of radiation field and personnel protection from leakage radiation. The capsule would then be selected under robotic control from its storage location, mounted on the arm of the SRIORT and moved into the proper position inside the patient in the proper location for irradiation. The physician would then move the capsule and proposed beam location to the angle and desired beam angle to the lesion. The SRIORT has a camera enabling direct visualization of the lesion. An alternate imaging device, appropriate for the tumor could be used in addition to a camera, such as an ultrasound transducer or probe. A laser could be mounted to identify and illuminate the spot of radiation beam application.

Traditional IORT using linear accelerators external to the body have used doses in the range of 10-20 Gy (Gy=gray=joule/kg energy deposited in matter by ionizing radiation). These doses can be delivered with a variety of devices and isotopes, most commonly those with high specific activity such as Ir-192 or Cs-137, or more recently x-ray diodes and solid state x-ray generators, can be used. In addition, other emitters such as Sr-90 (beta emitter with energy of 0.195 MeV). The table below gives examples of byproduct material and typical energies and half lives.

| Typical Isotope | Emission/Energy | Half Life |
|---|---|---|
| Cs-137 | Gamma/662 keV | 30 years |
| Ir-192 | Gamma/442 keV | 70.2 days |
| Sr-90 | Beta/195 keV | 29 years |
| Cf-252 | Neutron/fissile spectrum | 2.6 years |

Dose calculations are given by the following formula for isotopes:

$$\text{Dose} = (\Gamma_{AKR})(ISF)^2(\text{Strength})(\text{time of exposure})$$

These sources and other sources will generally have activity in the range of 5-10 Ci (10 Ci=370 GBq). For example, to deliver 20 Gy to a depth of 5 mm (4 mm+1 mm margin) for the 4 mm tumor shown in FIG. 1, from the applicator capsule, assuming a 10 Ci source strength, using Iridium-192, which has a specific air KERMA constant $$\left( \Gamma_{AKR} = \frac{(1.115 \, \mu Gy \times m^2)}{(GBq \times hr)} \right)$$

used to convert activity into dose, the following exposure would be required:

$$2000 \text{ cGy} = (370 \text{ GBq}) \frac{(111.5 \text{ cGy} - cm^2)}{(GBq - hr)} \left(\frac{1}{(0.25 \text{ cm})}\right)^2 \left(\frac{1 \text{ hr}}{60 \text{ min}}\right) t$$

which yields an exposure time of 2000/11001=0.181 minutes or 10 seconds exposure, assuming the above parameters. The quantity 0.25 cm. was selected in order to have a typical source to surface distance. Therefore, each lesion could be treated in under 1 minute, with precise control of exposures, field placement and size under real time guidance in the operating room using the SRIORT.

Due to the absolute criticality of distance in this exposure range, to delivered dose per unit time, the capsule will have an independent electronic distance measuring device using optical ranging.

Where organ motion is a concern, the device can be placed at an increased distance such as 0.5 cm from the tumor at the physician's discretion. Adjustments can be made to accommodate organ motion or relative motion of the patient. For this distance the above calculation would yield an exposure time of 0.67 minutes or 40.2 seconds.

The exposure time would be electronically controlled with a dual timer backup system whereby if the primary timer set time expires, then a backup secondary timer will engage and close the aperture to stop the radiation exposure. Both of these timers will have a clearly visual display at the operator's console with an alarm, both visual and audible when the cassette has radiation present and a second alarm both visual and audio if the cassette's control electronics fail to close the aperture (in the case of a radioactive source) or stop power to the radiation generator (in the case of an x-ray diode device).

The cassette's radiation "safe" chamber and aperture is constructed with radiation shielding in mind. Since the device is capable of using both high and low dose rate sources, shielding is mandatory for several reasons, the most important of which is to protect patient tissue from stray radiation emission from the device and to protect operating room personnel while the device or radiation source is in transit.

The shielding calculations are based on using either depleted uranium, lead or tungsten. Due to its superior shielding characteristics, the preferred shielding is uranium since uranium shielding will be thinner and allow for a more compact cassette which will be easier to insert into a laparoscopic wound (1-3 cm) and manipulate under robotic control, once it is inserted into the body. A typical source size (based on the Nucletron and Varian sources presently in use), is 0.5 mm in diameter by 5 mm long. To reduce the dose to acceptable levels during the time the source is in the patient, for this proposed calculation example, an assumption is made that a procedure with the source in the patient could last up to an hour. During this time the source will be emitting radiation and in the medical therapeutic use of radiation 60 cGy of exposure during a treatment can be administered at low risk. Since operating room personnel exposure must be kept lower than this, additional external shielding will be placed around the patient to meet ALARA radiation safety limits. The robotic workstation can be placed physically far from the patient, further minimizing the need for external shielding. The shielding calculation equation is $$10 \text{ Ci} \times \frac{37 \text{ GBq}}{\text{Ci}} \times \frac{111.5 \text{ cGy cm}^2}{\text{GBq} - \text{hr}} \times \left(\frac{1}{10 \text{ cm}}\right)^2 = 412.55 \text{ cGy/hr}$$

The 10 Ci is selected as the source strength. The quantity 37 GBq per Ci is a conversion factor. Ten centimeters is a typically selected distance to the patient body surface for the purpose of radiation shielding calculation because the average patient is approximately 20 cm. "thick." To reduce this dose rate to an acceptable level, the dose would be reduced to less than 60 cGy/hr or by a factor of approximately 1 or 2 tenth value layers of shielding. The tenth value layer of depleted uranium for Ir-192 is 6.5 mm so, 1.3 cm of depleted uranium will allow full shielding and reduce the leakage exposure rate at 10 cm from 411 cGy/hr to 4.1 cGy/hr at 10 cm or 16 cGy/hr at 5 cm. If tungsten were chosen, the shielding thickness required will be approximately 22 mm.

Given the source size, shielding requirements, and necessary electronics and adaptors, the preferred mode would be that the final dimensions of the cassette will be 4 cm in diameter×5 cm long or 4 cm×3 cm×5 cm. For the cone portion, if a cone is desired, the divergence of the cone should match the outer diameter of the tissue being irradiated. The cone can be selected in shape to correspond to the tumor shape. The cone can be very short, if used at all, 3 to 4 mm. The cassette can have varying cones mounted on it to conform to irregular tumor shapes. This will give adequate space to enclose a source, associated visualization, measurement and control electronics and mechanical safety apparatus. In SI units the shielding calculation equation is:

$$10 \text{ Ci} \times \frac{1000 \text{ mCi}}{\text{Ci}} \times \frac{4.111 \text{ cGy cm}^2}{\text{mCi} - \text{hr}} \times \left(\frac{1}{10 \text{ cm}}\right)^2 = 411 \text{ cGy/hr}$$

The shutter would have a diameter of at least the maximum field size desired. A cassette designed with a shutter opening of up to two cm. would be the most that would likely be required. The collimation of the radiation is more likely determined by the size of the source, but the shutter size should be larger than the largest desired collimation for a particular treatment regime.

A second mode of invention would use the cassette device as a positioning system only and for the delivery of radiation the device would have a transfer tube connector which would allow the use of existing High Dose Rate Remote afterloading devices such as the Nucletron HDR or Varian HDR device to provide the radiation source. These devices have an Ir-192 source similar to that described above which is attached to a cable and is positioned via transfer tubes which are attached to the HDR and the SRIORT cassette. This option would be available for institutions that have such a device available for interstitial radiotherapy. Other than the source delivery mechanism, in this case, the source is not an integrated part of the cassette, but rather delivered once the device is properly positioned. There are numerous disadvantages with this arrangement which make this less preferred than the self contained system, most notably is that the source is freely radiating while it traverses the transfer tubes, which will require all personnel to leave the operating room, thus dramatically increasing the time it takes to do the procedures.

The advantage of this device is that the device is small, easily manipulated by the SRIORT control systems, in real time, under direct visualization. This enables the surgeon and radiation oncologist to determine during the course of the operation areas of residual and unresectable disease and to deliver a dose of radiation precisely and interactively to sterilize the tumor. Because the capsule radiation source is orders of magnitude smaller than the conventional linear accelerator arms, it can be placed with high precision within the body and using articulating robotic "hands" holding the capsule in place, the field can be directed at the correct tumor site while inserted into the body through the robotic incisions.

Due to the potentially high activity sources in use, an emergency aperture closing mechanism incorporating both electronic and mechanical overrides would be used in the device. The system will also have fail safe mechanisms resulting in the aperture defaulting to the closed position absent electrical and mechanical signals to open the shutter or expose the aperture. In the case of x-ray generators, the fail safe will not permit current to flow to the device except under direct positive command.

In addition this device, by virtue of having a shielded capsule with a controllable aperture, together with the articulated robotic "wrist" or "hand" apparatus, allows precise positioning of the radiation source prior to opening the aperture and thus protecting normal tissue from radiation until the device is positioned and verified. This is a substantial advance over the current methods of applying intraoperative radiation therapy.

The purpose of using a shielded capsule is to minimize the damage to tissue while the capsule and the radiation source inside is in transit to the desired location. The capsule would be made of a high density shielding material such as lead, tungsten or uranium and the capsule would have a shutter covering an aperture through which radiation particles would be emitted. The shutter would also be of high density shielding material such as tungsten, but materials can be selected from those in the Berger & Seltzer handbook which contains data on mass energy attenuation coefficients sufficient to provide appropriate and necessary radiation protection. The capsule design will permit the adaptation of interchangeable shutters, much like the interchangeable lenses of a camera.

The interchangeable capsule would be stored in a shielded storage device, could be sterilized by steam or gas sterilization as is traditionally used in the operating room environment. The radiation source would be extracted from the storage pig, which is a larger, well shielded storage chamber used to transport and store radioactive source material, usually build of lead or tungsten, immediately adjacent to the patient in the operating room which will minimize the exposure of any personnel and the patient during the capsule transit time. It would be impractical to shield all gamma radiation from a source emitting gamma rays, but the distance allowed by the robotically assisted intraoperative radiation therapy applicator coupled with a reasonable amount of shielding would allow the device to be used while minimizing exposure to personnel to be in conformance with NCRP limits of exposures to radiation workers. The device will include adequate shielding in the form of mobile shielding units installed in the operating room to protect operating personnel in accordance with the ALARA—as low as reasonably achievable—philosophy of radiation protection and well below the accepted occupational exposure limits for the planned procedures. Survey instruments will be build into the apparatus and workstations to measure and record total in-room exposures. Mobile patient shielding would be available, depending on the radioisotope, to shield the patient, preferably with an aperture for the surgical entry site only so that any exposure of the patient is minimized. That mobile patient shielding could be in the form of one or a series of hooded containers such as lead shields on mobile casters, or a one or a series of lead aprons.

The cassette could be designed to either have contacts connected to internal wiring that meet control contacts on the robotic arm, or the internal wiring of the cassette can be connected by a wire harness to the robotic arm. An alternative preferred mode is a wireless control mechanism, but the level of ionizing radiation can be problematic.

For alpha or beta emitters, a lightweight capsule is possible. Under current technology a particle accelerator cannot be used for effective application of alpha particles, protons, electrons or light ions, which at energies useful therapeutically have a very short path length, but within that path length are devastating to the reproductive machinery of cancer cells (DNA and cellular ability to repair fractured DNA). Alpha particles and to a lesser extent, beta particles emitted from radioisotopes are readily obtained from a variety of isotopes, as are gamma rays. [Berger and Selzer, Affix]

Alpha particles are considered high linear energy transfer (LET) particles and deliver substantive damage to DNA in the form of double stranded DNA breaks, which are very difficult for cells to repair properly. Gamma rays, and x rays, in contrast are low LET particles and operate by the generation of radiolysis of water generating hydroxyl free radicals in the vicinity of DNA causing single strand and double stranded breaks following a linear-quadratic curve of cell survival v. dose, culminating in a loss of reproductive integrity of the cancer cells. Likewise beta particles, though low in linear energy transfer can cause double stranded breaks and destroy DNA through clusters of single stranded breaks which can be made permanent by oxygen fixation in non-hypoxic environments.

The capsule mounted on the SRIORT arm enables an alpha or beta emitter to be completely shielded from healthy tissue and to minimize transient damage as the radiation source is positioned at its intended target. Only on setting the aperture to the desired beam size, positioning the aperture in the correct location and desired angle and opening the shutter on the capsule will a beam of radiation be emitted through the aperture in the capsule in the desired direction to irradiate the lesion. In the case of an x-ray generator, the x-ray source will only be turned on when the above parameters are met.

As particle path length in tissue is very predictable, cancerous tissue can be destroyed with a much finer precision while minimizing damage to normal tissue, such as livers, kidneys and bowel. Sr-90 is a typical beta emitter which would be deadly to tissue without appropriate shielding, but when used in the proposed capsule could be safely directed to the targeted area. Likewise isotopes that emit alpha particles, and gamma rays or a source capable of developing x-rays can be used with appropriate shielding design on the capsule. The significant advantage of a beta emitter is enablement by the invention of a new technology of a very effective and predictable radiating isotope, and the miniaturization of the capsule because of reduction of bulk because shielding is much simpler. Any metal, or plastic such as lucite, with appropriate electron stopping power as set out in tables for a source available to a reasonably skilled practitioner, such as the tables in Berger & Seltzer, can be used for the shielding. Much smaller tumors in much smaller and confined spaces can be treated.

The capsule shutter could be simply the equivalent of a door occluding a radiation aperture. A preferred mode is to use an iris type aperture with a clam shell outer cover. The aperture can be opened to various diameters allowing the physician to choose the size of lesion to be treated and the surface area of the volume. A light source can be disposed on the exterior of the cassette for illumination inside the patient of the tumor to be irradiated. An alternate light source to act a a field light behind the aperture through which radiation will be emitted, but behind the iris would enable the physician to continue visible inspection of a lesion as he positions the device for maximum coverage of the tumor before the radiation source is opened by the clamshell. In addition, this mode gives redundant protection should one or the other of the apertures fail while the device is in place, thus allowing the device to be removed from the patient and safely deposited in the shielded pig until repairs can safely be made. A preferred light source is an LED, fiber-optic or solid state light emitter.

Upon completion of the treatment procedures, the SRIORT arm and radiation source can be remotely stored in the pig or appropriate storage device where sterilization and preparation for the next case can take place. For convenience sake, the storage device is preferably a table with a shielding container or pig on it. The storage device would likely have multiple pigs. The storage device including a shielding pig is referred to as a shielded source containment table, even if a closet or storage cabinet is used. To insure radiologic safety, each pig shall have a means of detecting radiation presence to insure that a source is present or absent from the pig. By regulation, that would usually be a room detector in the room, and/or a sensor inside the shielded source containment table, such as ion chamber, electrometer or Geiger-Mueller type device.

In addition to a radiation source, other devices could also be mounted with the unit, including a laser or particle emission device and used adjuvantly for tissue destruction. This device is not limited to the carriage of radioactive sources, but can also be used in conjunction with x-ray diodes or other radiation sources.

Because a surgical robot can have more than one arm, the invention enables more than one capsule to stand ready in the shielded source containment table so that should a physician determine to select a different capsule during irradiation, the capsule in present use can be quickly withdrawn, its path of extraction memorized and an new capsule with the preferred radiation source inserted.

Another important variations on the preferred mode relates to the doors or shutters on the capsule (also referred to as a cassette). The electromechanical movement could also be accomplished by hydraulic means with push pull pressure by an electrical signal to start a pump and then the mechanical action of pumping fluid to move a door. More specifically, a small hydraulic pump could be used to move the shutter or door, and a valve or a second pump used to move the shutter or door back. Also, the doors could be operated against nontoxic gas pressure so that when pressure is applied by a motor or hydraulically, in the event of power loss, the door moves to the closed position because the gas presses against the lost pressure.

The robotic system could be designed to combine the elements into an invention as before except that the non-radiation emitting features and associated control of emissions are separable from the radiation emitting features and associated control of emissions. By the expression "associated control of emissions" is meant the one or more doors or shutters on the capsule containing the radioisotope. As further description, on an effector arm or robot arm, or attachable to it, there would be a standard set of tools and carrier that would be used repeatedly. That will be referred to as the shuttle capsule holder. The capsule holding the radioactive source would be designed with necessary interconnects to control the doors to the shuttle capsule holder.

On the shuttle capsule holder could be other apparatus including tracking apparatus, range finders, laser pointer or camera/visualization apparatus. More specifically, those could be a stand-off remote detection for determining the distance from the radiation source to the tissue being irradiated, an electronic distance measuring device using optical ranging for locating the distance between said tissue being irradiated and said radioactive source, a means for utilizing ultrasonic detection to determine tissue depth, including tumor depth to determine an applicable margin to be irradiated, and one or more means for direct visualization by remote display of tissue adjacent to said capsule, which could be simply a fiber optic cable to transmit the image to an extra corporal screen or image capture device to see the image. The advantage of the direct visualization by remote means of tissue adjacent to said capsule is to ascertain if all diseased tissue has been surgically removed and to ascertain if further irradiation is necessary.

The procedure would be that the shuttle capsule holder would be set up by a technician and could have a range finder, light or laser pointer and other features pointed in U.S. Appl. 60/973,545, and 61/098,225 and PCT Appl. PCT/US2008/077100 entitled "DIRECT VISUALIZATION ROBOTIC INTRA-OPERATIVE RADIATION THERAPY APPLICATOR DEVICE." That shuttle capsule holder would be mounted to the robot, or picked up by the robot, and then remotely carried to the capsule for interconnection and then the dual system inserted into the body for treatment. Among the advantages are that capsule sizes can be smaller depending on which isotope/energy/emitter is selected and/or it enables tighter procedures and the shuttle capsule system allows reuse of the expensive components more easily.

Advantages of this system include the ability to use the more expensive parts repeatedly and to vary the capsules more easily. Capsules can be varied in size or protection depending on the isotope involved and perhaps the size of the incision. Also, the capsule can be shipped alone to a laboratory or radiopharmacy for reloading. The pig in which the capsule is stored could be shipped, the capsule filled with the hot radioisotope, and the pig returned to the hospital or surgical center to be opened by a robot and the operation to proceed as described.

The radioisotope can be mounted in the capsule any number of ways including gluing it on a pin in the capsule, or holding it in a ring like a circular gunsight or by otherwise securing it inside the capsule. The location should be secure and it is preferable it be known or measured because it is preferable to know where the radioisotope is exactly compared to the tumor being oblated. The size of the isotope varies in size and activity. Generally the order of magnitude is between 5-10 mm. For special purposes isotopes it may larger or smaller.

Another way of accomplishing the pickup of the capsule by a robot arm is to design the capsule so that it has a spine of contacts on it. Preferably to the rear of the capsule opposite the opening through which the radioisotope is exposed would be a group of contacts for electrical connection and any fiberoptic connection. Mounting them on a spine appears to be the easiest mode. The robot arm would have on its end a corresponding set of contacts and any fiberoptic connection interior to an alternately opening and closing jaw, and the jaw would be mounted on and then maneuvered on the robot arm or end effector to align the jaw's contacts with the group of contacts on the rear of the capsule and be closed on the contacts to make positive contact. The jaw could also be designed to be the shuttle capsule holder referred to before and/or to accomplish its functions. The jaw could be designed "inside out" particularly in the shuttle capsule holder design to have the contacts aligned inside a slot or aperture in the capsule into which is fitted a jaw which has the contacts on its exterior and is expanded to make positive contact. The jaw would preferably have material for attenuating radiation emissions similar to that of the capsule in order to preserve a relatively uniform radius of radiation attenuating material around the radioisotope.

Another preferred mode is to design a capsule in which is disposed a plunger. This mode would hold a "loose isotope", i.e. an unsealed radioactive source, in solution or in a form that is injectable into the tumor with a plunger from inside the capsule, enabling the use of a "hotter" isotope. This could be used with P-32 or I-131 or alpha or beta emitters,including Y-90.

EXAMPLES OF APPLICATIONS OF
PREFERRED MODE OF INVENTION

In the following two examples, a narrative description of how the SRIORT device and system will be used in actual practice. Several physicians will, of necessity be directly involved in these procedures due the the differences in training between the specialties. The key players in each case will be a surgeon and a radiation oncologist. The surgeon will be specifically trained in a pertinent area and the radiation oncologist is trained in the appropriate use, application and dosing of radiation for the treatment of tumors. In addition, a medical physicist, specifically trained in the use of radiation sources in conjunction with the radiation oncologist must be available for the planning of radiation delivery using the SRIORT device.

Example: Abdominal Tumor (Ovarian Cancer Stage IIIb)

Initially, the patient will be informed of the nature of the procedures to be performed in the treatment of the cancer. After being informed and after the patient acknowledges this information and gives her consent, the patient will be taken to the operating room and placed on the operating table in the supine position. Following this the patient will be anesthetized using general anesthesia supplied by the anesthesiologist.

After adequate general anesthesia is instilled, the patient will be examined under anesthesia to determine, if possible, the extent of disease. Following this, the patient will be prepped and draped in the usual sterile fashion and a subumbilical transverse incision will be made extending approximately 1-1.5 cm. Following this, a laparoscopic trochar with a TV camera in the bore will be advanced through the incision and under direct visualization into the peritoneal cavity. Following entry into the abdomen, the abdomen will be insufflated with carbon dioxide gas to distend the abdominal wall away from the intra-abdominal organs. Following this, again under direct visualization via the TV camera, a series of similar incisions will be made and trochars introduced into the abdomen which will allow the placement of robotic arms in the course of the surgery. Once these trochars are in place, the robotic actuating system will be placed into position at the operating table and the robotic arms will be placed in the ready position. The physicians will then move to the SRIORT control station, which will be located in the operating room behind a radiation shield of sufficient physical characteristics to provide as low as reasonably achievable radiation protection during the period of time that the intraoperative radiation device is in operation. The workstation will have visualization system originating from the robotic cameras placed in the patient, and selectable views. The control station will also have ergonomic robotic hand manipulators which will allow the physicians to move and manipulate the robotic arms in a natural way, under the control of computer and associated electronic circuitry.

The surgeon will then place the appropriate robotic arms into the patient via the previously placed trochars which will then be manipulated from the control station to perform the operation. The surgeon will generally use the robotic arms to place suction into areas of peritoneal fluid collections which will be sent to pathology for microscopic analysis for metastatic cancer cells. Following this, the abdomen will be washed with sterile water and that too will be collected and sent to pathology for analysis.

From this point, the surgeon will perform the hysterectomy, bilateral salpingo-oopherectomy and pelvic and para-aortic lymph node dissections. Once this part of the procedure is complete, the surgeon will turn his attention to the remainder of the abdomen. Generally in locally advanced ovarian cancer, the omentum is also removed. Following this, the surgeon will inspect the remainder of the bowel using the robotic devices and cameras for further evidence of cancer. S/he will examine the bladder, rectum, bowel, peritoneal surfaces, the liver and the underside of the diaphragm. If lesions are found, the surgeon will resect, to the greatest extent possible, any visible disease within the peritoneum, using the robotic surgery system. During the debulking process, the surgeon using the SRIORT system will activate a marking device which will record the spatial coordinates of all sites of known or suspected cancer that has been identified and/or resected within the abdomen or surgical field. These coordinates will then be available to identify, post-operatively and in future procedures, potential locations where further radiation therapy might be considered for the treatment of microscopic disease.

The marking device will consist of an electronic control which will signal the control computers to record the present spatial position and settings of the robotic arm, viewing system and controls to, in essence, create a stored anatomical "waypoint" allowing the surgeon to select the location at some point in the future, display the waypoint on the operating room imaging monitors either alone or overlaid on the pre-operative imaging. This will allow the surgeon and the radiation oncologist to return to the area of interest in the patient for further study, irradiation or procedures. In addition, the device will allow the surgeon to place a gold seed marker in tissue to identify the suspect tissue radiologically at a future point, post-operatively. Adjustments could be made to waypoints during surgery to accommodate changes in position.

Once the surgeon has completed his work, the radiation oncologist, in cooperation with the surgeon will place on monitors in the operating theatre the pre-operative medical imaging, including, but not limited to computed tomography scans (CT/CAT), positron emission tomography scans (PET or PET/CT), magnetic resonance imaging scans (MRI), ultrasonic imaging and any other imaging techniques which may be helpful in localizing position and radiation within the patient. Once the surgeon and the radiation oncologist determine the sites to be irradiated, the radiation oncologist, in consultation with the medical physicist, the shielding equipment will be moved into place in the operating theatre to protect personnel necessary to the operation from the radiation sources used in the treatment of the lesions.

Following this, a cart containing the SRIORT robotic applicator arms capable of attaching cassettes containing the radiation sources, along with the cassettes and radiation sources will be brought into the operating theatre.

Once the radiation oncologist has selected the appropriate radiation sources and doses to be used in the treatment of lesions, the medical physicist will pre-program the SRIORT device using a separate computer workstation to identify the sources to be used, the beam size to be used and the depth of irradiation and doses of radiation to be delivered. Once these parameters have been programmed into the device, the delivery of the radiation can then proceed.

Typically, as is presently done, for instance in prostate seeding, once the lesions are marked, a simulation of the proposed procedure would be performed. Techniques of radiation simulation that are presently available would be incorporated in programming of a general purpose computer used in conjunction with the system.

The radiation oncologist will select the appropriate arm to be used and will, using the SRIORT device move the arm into position to extract the selected cassette from the radiation source storage cart (pig, in the case of a radionuclide source). The cassette will have electrical connections which will enable the cassette to identify itself to the SRIORT manipulator and hence back to the control station. The SRIORT will compare the cassette identification with the pre-programmed source selection and radiation dose planning previously done by the physicist to insure that the proper cassette has been mounted with the correct source. The source, while still in its shielded chamber (pig) will then have its aperture set to a specific set of sizes and each size will be measured to verify the accuracy of the aperture size controls prior to extraction. The shutter will then be opened, as well to expose a radiation detector to verify the source activity/strength matches the predicted values calculated and referenced in the pre-programmed controller. This will allow the radiation oncologist and the physicist to resolve any discrepancies prior to actually introducing the device into a patient.

Once verification of the planning and exposure parameters have taken place, the SRIORT control system will allow the physician to remove the cassette and manipulate the robotic arm carrying the cassette into position within the patient via the appropriate trochar. The cassette will also contain a locator transducer which will identify its precise spatial location within the operating theatre and more importantly within the patient. This location will also be transmitted to the imaging workstations containing the medical images and the location of the radiation source within the patient can be depicted on the operating room monitors, as well as directly visualized within the patient on the SRIORT vision system. While this will generally be done with visual spectrum of light, it will also be possible to map non-visual spectrum such as infrared spectra to the visible spectrum to allow the radiation oncologist to observe physiologic activity which might not be observable with ordinary visible light, thus enhancing the physician's ability to identify and treat areas of potential residual cancer and prevent recurrences.

Under these visualization schemas, the physician from the SRIORT control station will advance the radiation cassette into the proper position to deliver the radiation to the intended target. The radiation oncologist will then set an aperture size appropriate to treat the lesion, and then visually identify this aperture by means of a self contained field light which will replicate the actual radiation field through the aperture. Comparing this field light with the area of interest, the physician, in real time will make fine adjustments to the position of the source and aperture size to conform precisely to the area to be irradiated. The field light can be supplemented with an aiming laser device attached to the cassette or the SRIORT arm carrying the cassette.

Once this is done, the SRIORT will perform final exposure rate and time calculations and the shutters will be opened, allowing the cassette's radiation source to irradiate the lesion to the dose and depth desired for proper disease control. The radiation oncologist will have the ability to review and examine directly by manipulation of the SRIORT to the previously stored coordinates of areas of interest, the imaging studies and via direct visible and extra-visual spectral mapping information.

This process will be repeated as many times as is necessary to properly treat each and every lesion identified for the best hope of permanent eradication of the cancerous lesions. In each case, the radiation oncologist and the medical physicist will have the ability to select from a variety of cassettes, the appropriate intra-operative radiation applicator for each lesion to be treated with radiation at the time of the surgery and to manipulate and program the sources in real time for the best possible chance of cure of cancer and neoplastic diseases.

In the case of other sites, such as the head and neck, brain or chest, these procedures described above will be equally applicable, with appropriate modifications for the site of disease. This SRIORT device will permit the use of radiation to treat areas previously untreatable intraoperatively due to the inability to position accelerators precisely. Other devices, such as Med-Tech's brachytherapy intraoperative applicator, are incapable of the precision necessary to spot treat lesions of interest without causing unacceptable morbidity for lesions located on or adjacent to radiosensitive organs.

While the invention has focused on a procedure relating to incision surgery and resection of tissue, and follow-up by irradiation to achieve adequate margins, the invention is applicable to surgery where resection is deemed undesirable, such as so-called "inoperable cancers." These involve lesions which for instance are adjacent to the aorta where resection has too high a risk of mortality. This invention enables a stand-off from a critical vessel or organ, and use of irradiation, potentially in a step-by-step manner, to destroy tissue iteratively, avoiding physical contact with the radiosensitive tissue, and/or permitting healthy tissue to grow back.

Another variation is to utilize a sensor on a moving organ or in conjunction with a moving organ and coordinate the output from that sensor with the opening and closing of the shutter and aperture, and the positioning of the capsule. Thus, for a lesion on heart tissue, an EKG lead could be connected and integrated with a general purpose computer so that radiation exposure would be timed to only occur at certain points in the relative movement of tissue vis a vis the capsule. Alternatively, a range finder, either visual, optical, or ultrasonic, on the capsule could be coordinated with the aperture so that radiation exposure occurred only in certain distance ranges. This would enable certain heart and pulmonary-aortic lesions to be treated by a stand-off tissue irradiation with considerably less danger to a patient. The capsule could be moved in conjunction with rhythmic tissue movement.

The invention can be used, for example, in conjunction with intraparenchymal lesions in the liver. The liver is radiosensitive tissue and the intraparenchymal lesions are not ordinarily amenable to radiation therapy without lethal consequences.

The invention enables stereotactical radiosurgery type techniques where the physician can, in real time, determine the depth of effect of irradiation, and make real time adjustments in dosages, hopefully eliminating another invasion of the patient's body.

The invention contemplates a means for positive attachment of the capsule by which is meant that the robot arm has a clasp, finger, bayonet, clamp or slide mechanism to positively lock the capsule, and further, has an electrical feedback mechanism that operates only when positive lock has occurred meaning the capsule is securely attached to the robot arm. A means for positive attachment also includes a surgical end effector as defined in U.S. Pat. No. 6,246,200 cited earlier.

The invention contemplates that other arms of the surgical robot may be engaged in surgery, or in tissue manipulation to facilitate entry of the capsule for irradiation.

If multiple consoles are contemplated, prior art describes and this invention would use an arbitration mechanism to preferably give priority at all times to the handling of the capsule containing a radioactive substance absent a specific command to the contrary.

Potentially a speech interface could be included to assist in direction on pre-defined axes, but it is important to remember of radiologic safety reasons, close manual override and control is needed.

While the preferred mode of electrical communication and control is a physical electrical electrical connection and control by pins on the capsule against contacts on the robot arm or vice versa, another mode of invention is to use telecommunication between the surgical robot, or to the surgical robot, and/or telecommunication to the capsule.

The term means for imaging is intended to include CT (computer tomography), MRI (magnetic resonance imaging), ultrasound or ultrasonic imaging; functional MRI, PET (positive emission tomography), PET/CT and nuclear medical scanning.

The term means for direct visualization or direct visualization includes the use of visible infrared and ultraviolet light or any combination of those to enable direct visualization.

Also proposed is the concept of placing two means of direct visualization enabling true internal stereoscopic visualization through more than one mounted means for direct visualization on the capsule.

The term means for direct visualization or direct visualization includes the use of visible, infrared and ultraviolet light or any combination of those to enable direct visualization, including an endoscope or a laparascope.

Also proposed is the concept of placing stereoscopic endoscope or stereoscopic laparascope, meaning two means of direct visualization enabling true internal stereoscopic visualization through more than one mounted means for direct visualization on the capsule.

The term "stand-off remote detection" includes radar and electric signaling for determining distance; in this invention the stand-off remote detection is primarily intended to determine the distance from the radiation source to the tissue being irradiated, taking into account the tare length of the radiation source to the edge of the capsule, or the end of the shroud if one is used. Other forms of stand-off remote detection are also discussed such as ultrasound and laser optical finders.

A fail-safe closed position means that if power is lost, particularly power to operate the shutter, the shutter closes occluding the aperture through which radiation is being emitted into the patient.

The embodiments represented herein are only a few of the many embodiments and modifications that a practitioner reasonably skilled in the art could make or use. The invention is not limited to these embodiments. Alternative embodiments and modifications which would still be encompassed by the invention may be made by those skilled in the art, particularly in light of the foregoing teachings. Therefore, the following claims are intended to cover any alternative embodiments, modifications or equivalents which may be included within the spirit and scope of the invention as claimed.

REFERENCES

Attix, Frank H, Introduction to Radiologic Physics and Radiation Dosimetry, John Wiley & Sons, 1986

Berger & Seltzer, Tables of Energy Losses and Ranges of Electrons and Positrons, NASA, 1964 Gunderson & Tepper, Clinical Radiation Oncology, $2^{nd}$ Edition, Chapter 15, Intraoperative Irradiation, pp 315-328

Haddock M G, Petersen I A Webb M J: Intraoperative Radiotherapy for locally advanced gynecologic malignancies, Frontiers of Radiation Therapy Oncology, 31:356-259; 1997

Khan, Faiz: The Physics of Radiation Therapy, 1984, Williams & Wilkins, Baltimore, ISBN 0-683-04501-6

Petersen, I A, Haddock, M G, Donohue, J H: Use of intraoperative Electron Beam Radiotherapy in the Management of Retroperitoneal Soft Tissue Sarcoma, Int. J. Radiat Oncol Biol Phys 50:126-131, 2001

Ramsay J, Suit H D: Experimental Studies on the incidence of metastases after failure of radiation treatment and the effect of salvage surgery. Int. J. Radiat Oncol Biol Phys 14:1165-1168;1988

Stump, K E, DeWerd, L A, Micka, J A, and Anderson, D R: Calibration of New HDR Ir-192 Sources. Med Physics, Vol 29(7):1483-1488

Suit H D: Local control in patient survival. Int. J. Radiat Oncol Biol Phys 23:653-660, 1992

Suit H D: Potential for improving survival rates for the cancer patient by increasing efficacy of treatment of the primary lesion. Cancer 50:1227-1234, 1982

Swiss Society for Radiobiology and Physics, Dosimetry and Quality Assurance in High Dose Rate Brachytherapy with Iridium-192, Recommendation #13, January, 2005, ISBN 3908-125-36-7

We claim:

1. A surgical robotic intra-operative radiation therapy device comprising:

a robotic device capable of surgical use having at least one robotic arm which can be manipulated remotely;

for a patient having a surgical incision, an interchangeable capsule for irradiating said at least one tissue, said capsule for irradiating said at least one tissue and said incision being sized for said capsule to be insertable through said surgical incision;

said capsule having an aperture opening to a cavity internal to said capsule, said capsule having a shutter for alternately occluding and uncovering said aperture opening to said cavity, and said capsule being mountable on said robotic arm;

said robotic arm having a first means for robotic arm electrical communication and control;

said capsule having a second means for electrical communication and control compatible for purposes of interchangeability with said means for robotic arm electrical communication and control;

a means for positive attachment between said robotic arm and said capsule, said means for positive attachment being compatible for purposes of interchangeability with said robotic arm and said first and second means for electrical communication and control;

said cavity internal to said capsule and thereby interior to said aperture being sized to contain a radioactive source for irradiating patient tissue;

said capsule having shielding selected to attenuate radiation exterior to said capsule; and a remotely operable means for controlling said shutter;

said shutter having a fail-safe closed position;

said intraoperative surgical device having said at least one remotely manipulatable robot arm cooperating with said capsule to move said aperture of said capsule adjacent to patient tissue to be irradiated, so that by operating said electromechanical control, said shutter can be opened to expose said patient tissue to a radiation source disposed within said capsule.

2. The surgical robotic intra-operative radiation therapy device according to claim 1, further comprising:

a general purpose computer for transmitting data to and from said capsule, said computer being programmed to provide logic, and to implement motion, timing, visualization, irradiation and position reporting functions for said device.

3. The surgical robotic intra-operative radiation therapy device according to claim 2, further comprising:
said capsule having an adjustable aperture size.

4. The surgical robotic intra-operative radiation therapy device according to claim 2, further comprising:
a shroud to narrow a beam of radiation emanating from said capsule through said shutter.

5. The surgical robotic intra-operative radiation therapy device according to claim 4, further comprising:
said capsule having an adjustable aperture size.

6. The integrated surgical robotic intra-operative radiation therapy system according to claim 2, further comprising:
at least one means for direct visualization by remote means of tissue adjacent to said capsule to ascertain if all diseased tissue has been surgically removed and to ascertain if further irradiation is necessary.

7. The surgical robotic intra-operative radiation therapy device according to claim 6, further comprising:
said capsule having an adjustable aperture size.

8. The surgical robotic intra-operative radiation therapy device according to claim 6, further comprising:
a shroud to narrow a beam of radiation emanating from said capsule through said shutter.

9. The surgical robotic intra-operative radiation therapy device according to claim 8, further comprising:
said capsule having an adjustable aperture size.

10. The surgical robotic intra-operative radiation therapy device as in one of claims 1 through 9, further comprising:
a means for utilizing ultrasonic detection to determine tissue depth, including tumor depth to determine an applicable margin to be irradiated.

11. The surgical robotic intra-operative radiation therapy device as in one of claims 1 through 9, further comprising:
at least one means for direct visualization by remote display of tissue adjacent to said capsule.

12. The surgical robotic intra-operative radiation therapy device as in one of claims 1 through 9, further comprising:
a selected radiation source in said cavity of said capsule appropriate to irradiate said tissue;
said capsule being selected to attenuate radiation based on its shielding characteristic for said selected radiation source to excess doses of radiation to said patient while said shutter is in said closed position for the time period said capsule is proposed to be inside said patient.

13. The surgical robotic intra-operative radiation therapy device as in one of claims 1 through 9, further comprising:
a speech interface subject to manual override to enable voice recognition of an operator of said device to assist in direction of said capsule on pre-defined axes, said speech interface being integrated with said general purpose computer.

14. The surgical robotic intra-operative radiation therapy device as in one of claims 2 through 9, further comprising:
an electronic distance measuring device using optical ranging for locating the distance between said tissue being irradiated and said radioactive source.

15. The surgical robotic intra-operative radiation therapy device as in one of claims 2 through 9, further comprising:
stand-off remote detection for determining the distance from the radiation source to the tissue being irradiated.

16. An integrated surgical robotic intra-operative radiation therapy system comprising:
a means for display of medical imaging of at least one tissue of a patient, said means for display being visible to an operator of said system;
at least one robotic arm which can be manipulated remotely;
for a patient having a surgical incision, an interchangeable capsule for irradiating said at least one tissue, said capsule for irradiating said at least one tissue and said incision being sized for said capsule to be insertable through said surgical incision;
said capsule having an aperture opening to a cavity internal to said capsule, said capsule having a shutter for alternately occluding and uncovering said aperture opening to said cavity, and said capsule being mountable on said robotic arm;
said at least one robotic arm having a first means for robotic arm electrical communication and control;
said capsule having a second means for electrical communication and control compatible for purposes of interchangeability with said means for robotic arm electrical communication and control;
a means for positive attachment between said at least one robotic arm and said capsule, said means for positive attachment being compatible for purposes of interchangeability with said at least one robotic arm and said first and second means for electrical communication and control;
said cavity internal to said capsule and thereby interior to said aperture being sized to contain a radioactive source for irradiating patient tissue;
said capsule having shielding selected to attenuate radiation exterior to said capsule; and
an electromechanical control for said shutter;
said shutter having a remotely operable means for controlling said shutter;
said shutter having a fail-safe closed position;
a shielded source containment table arrayed adjacent to said patient;
mobile patient shielding;
said robot arm which can be manipulated remotely being integrated through said integrated surgical robotic intra-operative radiation therapy system to remove said capsule from said shielded source containment table, and thereafter, in cooperation with capsule, to move said aperture of said capsule adjacent to at least one patient tissue to be irradiated, so that by operating said electromechanical control, said shutter can be opened to expose said patient tissue to a radiation source disposed within said capsule.

17. The integrated surgical robotic intra-operative radiation therapy system according to claim 16, further comprising:
a means for utilizing ultrasonic detection to determine tissue depth, including tumor depth to determine an applicable margin to be irradiated.

18. The surgical robotic intra-operative radiation therapy device according to claim 17, further comprising:
said capsule having an adjustable aperture size.

19. The surgical robotic intra-operative radiation therapy device according to claim 17, further comprising:
a shroud to narrow a beam of radiation emanating from said capsule through said shutter.

20. The surgical robotic intra-operative radiation therapy device according to claim 19, further comprising:
said capsule having an adjustable aperture size.

21. The integrated surgical robotic intra-operative radiation therapy system according to claim 16, further comprising:
a general purpose computer for transmitting data to and from said capsule, said computer being programmed to provide logic, and to implement motion, timing, visualization, irradiation and position reporting functions for said device.

22. The surgical robotic intra-operative radiation therapy device according to claim 21, further comprising:
said capsule having an adjustable aperture size.

23. The surgical robotic intra-operative radiation therapy device according to claim 21, further comprising:
a shroud to narrow a beam of radiation emanating from said capsule through said shutter.

24. The surgical robotic intra-operative radiation therapy device according to claim 23, further comprising:
said capsule having an adjustable aperture size.

25. The integrated surgical robotic intra-operative radiation therapy system according to claim 21, further comprising:
a means for utilizing ultrasonic detection to determine tissue depth, including tumor depth to determine an applicable margin to be irradiated.

26. The surgical robotic intra-operative radiation therapy device according to claim 25, further comprising:
said capsule having an adjustable aperture size.

27. The surgical robotic intra-operative radiation therapy device according to claim 25, further comprising:
a shroud to narrow a beam of radiation emanating from said capsule through said shutter.

28. The surgical robotic intra-operative radiation therapy device according to claim 27, further comprising:
said capsule having an adjustable aperture size.

29. The integrated surgical robotic intra-operative radiation therapy system according to claim 21, further comprising:
means for locating and recording a waypoint for re-visitation at the close of initial traditional resection surgery to enable rapid re-visitation and medical examination of particular tissue to determine if irradiation is appropriate.

30. The surgical robotic intra-operative radiation therapy device according to claim 29, further comprising:
said capsule having an adjustable aperture size.

31. The surgical robotic intra-operative radiation therapy device according to claim 29, further comprising:
a shroud to narrow a beam of radiation emanating from said capsule through said shutter.

32. The surgical robotic intra-operative radiation therapy device according to claim 31, further comprising:
said capsule having an adjustable aperture size.

33. The integrated surgical robotic intra-operative radiation therapy system according to claim 21, further comprising:
a means for locating the three-dimensional coordinates of medical imaging on said patient relative to said robot arm;
a means for identifying and tracking the three-dimensional coordinates in real time of said capsule within the body and displaying the location of said capsule within the body relative to said at least one tissue to be irradiated in said patient.

34. The surgical robotic intra-operative radiation therapy device according to claim 33, further comprising:
said capsule having an adjustable aperture size.

35. The surgical robotic intra-operative radiation therapy device according to claim 33, further comprising:
a shroud to narrow a beam of radiation emanating from said capsule through said shutter.

36. The surgical robotic intra-operative radiation therapy device according to claim 35, further comprising:
said capsule having an adjustable aperture size.

37. The integrated surgical robotic intra-operative radiation therapy system according to claim 33, further comprising:
said general purpose computer being enabled to accept input of data on the radioactive characteristics of said selected radioactive source, to accept input of type of tissue being irradiated, to accept input of data on the distance of said source from said tissue being irradiated, to accept input of data on the length of time said shutter is in the open position, to accept input of ambient radiation information, and to output display real time radiation field distribution on said display means; and
said general purpose computer determining a desired margin relative to said tissue to be irradiated, automatically positioning said capsule, and based on said margin, output of said means for locating and said means for means for identifying and tracking the three-dimensional coordinates of said capsule, opening said shutter, and setting stop-limits for said opening of said shutter in order to irradiate said tissue.

38. The surgical robotic intra-operative radiation therapy device according to claim 37, further comprising:
said capsule having an adjustable aperture size.

39. The surgical robotic intra-operative radiation therapy device according to claim 37, further comprising:
a shroud to narrow a beam of radiation emanating from said capsule through said shutter.

40. The surgical robotic intra-operative radiation therapy device according to claim 39, further comprising:
said capsule having an adjustable aperture size.

41. The integrated surgical robotic intra-operative radiation therapy system according to claim 37, further comprising:
at least one means for direct visualization by remote display of tissue adjacent to said capsule.

42. The surgical robotic intra-operative radiation therapy device according to claim 41, further comprising:
said capsule having an adjustable aperture size.

43. The surgical robotic intra-operative radiation therapy device according to claim 41, further comprising:
a shroud to narrow a beam of radiation emanating from said capsule through said shutter.

44. The surgical robotic intra-operative radiation therapy device according to claim 43, further comprising:
said capsule having an adjustable aperture size.

45. The integrated surgical robotic intra-operative radiation therapy system according to claim 37, further comprising:
a means for utilizing ultrasonic detection to determine tissue depth, including tumor depth to determine an applicable margin to be irradiated.

46. The surgical robotic intra-operative radiation therapy device according to claim 45, further comprising:
said capsule having an adjustable aperture size.

47. The surgical robotic intra-operative radiation therapy device according to claim 45, further comprising:
a shroud to narrow a beam of radiation emanating from said capsule through said shutter.

48. The surgical robotic intra-operative radiation therapy device according to claim 47, further comprising:
said capsule having an adjustable aperture size.

49. The integrated surgical robotic intra-operative radiation therapy system according to claim 37, further comprising:

an electronic distance measuring device using optical ranging for locating the distance between said tissue being irradiated and said radioactive source.

50. The surgical robotic intra-operative radiation therapy device according to claim 49, further comprising:
said capsule having an adjustable aperture size.

51. The surgical robotic intra-operative radiation therapy device according to claim 49, further comprising:
a shroud to narrow a beam of radiation emanating from said capsule through said shutter.

52. The surgical robotic intra-operative radiation therapy device according to claim 51, further comprising:
said capsule having an adjustable aperture size.

53. The integrated surgical robotic intra-operative radiation therapy system according to claim 37, further comprising:
stand-off remote detection for determining the distance from the radiation source to the tissue being irradiated.

54. The surgical robotic intra-operative radiation therapy device according to claim 53, further comprising:
said capsule having an adjustable aperture size.

55. The surgical robotic intra-operative radiation therapy device according to claim 53, further comprising:
a shroud to narrow a beam of radiation emanating from said capsule through said shutter.

56. The surgical robotic intra-operative radiation therapy device according to claim 55, further comprising:
said capsule having an adjustable aperture size.

57. The integrated surgical robotic intra-operative radiation therapy system according to claim 37, further comprising:
means for locating and recording a waypoint for re-visitation at the close of initial traditional resection surgery to enable rapid re-visitation and medical examination of particular tissue to determine if irradiation is appropriate.

58. The surgical robotic intra-operative radiation therapy device according to claim 57, further comprising:
said capsule having an adjustable aperture size.

59. The surgical robotic intra-operative radiation therapy device according to claim 57, further comprising:
a shroud to narrow a beam of radiation emanating from said capsule through said shutter.

60. The surgical robotic intra-operative radiation therapy device according to claim 59, further comprising:
said capsule having an adjustable aperture size.

61. The integrated surgical robotic intra-operative radiation therapy system as in one of claims 16 through 60, further comprising:
in a patient having tissue to be irradiated, a selected radiation source in said cavity of said capsule appropriate to irradiate said tissue;
said capsule being selected to attenuate radiation based on its shielding characteristic for said selected radiation source to excess doses of radiation to said patient while said shutter is in said closed position for the time period said capsule is proposed to be inside said patient.

62. The surgical robotic intra-operative radiation therapy device as in one of claims 21 through 60, further comprising:
a speech interface subject to manual override to enable voice recognition of an operator of said device to assist in direction of said capsule on pre-defined axes, said speech interface being integrated with said general purpose computer.

* * * * *